United States Patent [19]

Beyreuther et al.

[11] Patent Number: 4,459,983
[45] Date of Patent: Jul. 17, 1984

[54] BREATHING APPARATUS FOR REANIMATION OF NEWBORNS

[75] Inventors: Christian Beyreuther, Rechnerstrasse 26, 8013 Haar, Fed. Rep. of Germany; Klaus Riegel, Munich, Fed. Rep. of Germany

[73] Assignee: Christian Beyreuther, Haar, Fed. Rep. of Germany

[21] Appl. No.: 247,300

[22] PCT Filed: Jul. 23, 1980

[86] PCT No.: PCT/EP80/00062

§ 371 Date: Mar. 23, 1981

§ 102(e) Date: Mar. 23, 1981

[87] PCT Pub. No.: WO81/00212

PCT Pub. Date: Feb. 5, 1981

[30] Foreign Application Priority Data

Jul. 24, 1979 [DE] Fed. Rep. of Germany ....... 2929996
Jul. 21, 1980 [DE] Fed. Rep. of Germany ....... 3027614

[51] Int. Cl.³ .............................................. A61M 16/00
[52] U.S. Cl. ........................... 128/205.24; 128/205.25; 137/247.17; 137/251; 251/315
[58] Field of Search ...................... 128/204.18, 204.21, 128/204.23, 205.18, 205.23, 205.24, 200.11; 137/247.17, 247.35, 247.41, 251, 253; 251/315

[56] References Cited

U.S. PATENT DOCUMENTS

| | | | |
|---|---|---|---|
| 2,613,908 | 10/1952 | Palen | 251/315 |
| 2,989,069 | 6/1961 | Nixon | 137/251 |
| 3,036,589 | 5/1962 | Mosier | 251/315 |
| 4,011,866 | 3/1977 | Klein et al. | 128/204.21 |
| 4,030,492 | 6/1977 | Simbruner | 128/205.24 |
| 4,171,697 | 10/1979 | Arion | 128/205.24 |

FOREIGN PATENT DOCUMENTS 136664 12/1919 United Kingdom ................ 137/251

OTHER PUBLICATIONS

K. Riegel et al., 99 *German Medical Weekly*, (1974), 1624–1626.

*Primary Examiner*—Henry J. Recla
*Attorney, Agent, or Firm*—Scully, Scott, Murphy & Presser

[57] ABSTRACT

An apparatus (B) for reanimating new-born children with at least two stages provided with an inhaling pressure controlling device. In this apparatus during breathing by blowing pressure, a breathing is possible according to "IPPV + PEEP and CPAP". The breathing apparatus (B) is of a simple construction and affords high safety for the patient. The breathing apparatus (B) has in a first breathing stage a water column (2) the maximum pressure of which corresponds to the maximum inhaling pressure. In the second breathing stage, a choke is connectable to the water column (2) of the first stage. In one embodiment the choke (6) is removable, in another embodiment it is made of a water column (32) connected in series. With the second stage higher limited blowing pressures may be used for the lungs. In order to obtain a constant static pressure upon expiration and a positive pressure at the end of expiration it is possible to secure on the expiration opening (5,23) of the patient's adaptator (4) another choke (6,6') which may be identical to the second stage choke.

17 Claims, 8 Drawing Figures

BREATHING APPARATUS FOR REANIMATION OF NEWBORNS

The present invention relates to a breathing apparatus for the reanimation of newborn infants, including a water column serving as an inhalation valve, with a T-connector member attached to the riser tube of the water column, by means of which the water column is connected through breathing hoses with a breathing gas source and with a patient adapter, which includes a free closable opening for exhalation in communication with the atmosphere, in which the quantity of the breathing gas introduced from the breathing gas source is adjustable through a regulator, wherein the maximum immersed depth of the riser tube determines the maximum inspiratory breathing pressure for which the closing period of the exhaling opening determines the breathing frequency and breathing phase.

The most important event after birth is the commencement of the pulmonary gas change, in effect, the inherent lung breathing (spontaneous breathing) of the newborn infant. The extended primary apnoe (breathing stoppage) is the most important intermediate case. It is predicated on a paralysis of the breathing center through a lack of oxygen during the birth or because of narcotics which have been given to the mother prior to or during the birth. This extremely dangerous condition must be eliminated without delay through reanimation. An airation of the lungs of the newborn infant which is not rapid produces the most serious adaptability and development difficulties to the child. As a rule, in this acutely dangerous condition, an instant initial blowing up of the lungs with compromised oxygen for a duration of presently 10-15 seconds, a so-called blow pressure breathing, leads through an unfolding of the alveolas, rapidly to the intended spontaneous breathing.

In particular for premature newborn infants (premies), not infrequently the breathing must additionally be supported over a lengthy period of time. An important sign of the premature infant is the lack of a sufficient quantity of surface active substance, the so called lack of surfactant syndrom, or idiopathic breathing emergency syndrom. The result is that, during each exhalation phase (expiration), due to the inadequately reduced surface tension, alveolas will collapse. Collapsed alveolas, however, can no longer take part with the breathing gas change. The blood is under-saturated with oxygen. This lack of oxygen leads in an increasing measure to breathing difficulty and finally, through paralysis of the breathing center to a breathing stoppage when there is not timely prevented that the collapsing pressure in the alveolas be distrupted. For support of the breathing during idiopathic breathing emergency syndrom, in recent times there has been utilized a breathing procedure with great success, which constantly maintains a continuous positive pressure (CPAP) of up to about 15 cm $H_2O$ in the breathing passages, which is directed counter to the alveolar collapse, the socalled CPAP breathing. An early consequential application of this method immediately after the birth upholds the spontaneous breathing, and thus saves such children from more intensive breathing techniques with their not inconsiderable side effects.

Nevertheless, if the newborn shows signs of an increasing breathing emergency, the breathing cycle must be timely artificially imitated by means of a breathing apparatus. Thereby, periodically, within the inhalation phase (inspiration) there is produced a positive pressure for the blowing up (IPPV), and in the exhalation phase, a positive end expirational pressure (PEEP) maintained above the collapsing pressure of the aveolas; there is effectuated the socalled IPPV+PEEP breathing. The lower pressure limit (PEEP) hereby corresponds to the pressure during the CPAP breathing, the upper however, not to the initial blowing pressure breathing required. The initial unfolding of the lungs, in essence, generally demands a higher breathing pressure than would be necessary for maintaining the breathing.

It is demanded of a breathing apparatus for newborn infants with the major utilization thereof in birth clinics and during transport into a childrens clinic that, in a simple and dependable manner it can be controllably adapted to these requirements for aiding the breathing of newborn infants. Eliminated hereby can be an automation of the breathing procedures since, on the one hand, the initial blowing pressure breathing, conformed to the individual needs, is undertaken by hand, and, the CPAP breathing after stabilized spontaneous breathing no longer requires any kind of control and, on the other hand, the cycle of the newborn which is still extremely unstable after birth demands an individual and flexible therapy orients itself to the rapidly changing conditions, which therapy is best afforded directly through hand-assisted breathing. The automatically controlled breathing at respiratorial insufficient is hereby first obtainable during stationary treatment. Furthermore, there must be required an uncomplicated construction and easy setting of the breathing apparatus so as to avoid unintended erroneous operations, and further with this construction, in the breathing techniques applied to infants, inexperienced personnel will be able to cope without risk. An experienced pediatrician is even today seldom available. One of the greatest dangers which threatens the newborn infant, namely through an erroneously set breathing pressure, is that of lung rupture with pneumothorax. As a relatively safe inspiratoric breathing pressure limits there should be those up to a maximum of 30 cms $H_2O$ (cm water column). For the initial unfolding of the lung, however, it may be necessary have blowing pressures of up to 70 cm $H_2O$ whereas, conversely, at a previously damaged lung a pressure of 30 cm $H_2O$ can already lead to the feared lung rupture. This signifies that the treating personnel must stepwise work up to the individually required and still tolerable breathing pressure which represents the critical key magnitude in the breathing of newborn infants. Its simple, errorless and controllable adjustment must be assured. All other breathing parameters are, in contrast thereto, only of secondary significance.

Known are breathing apparatuses for newborn infants with an automatic time control device (German Published Patent Application No. 2 405 955) which can also be operated manually. These apparatuses are in connection with the patient through two breathing hoses, supplying the breathing gas and returning the breathing gas. Both breathing hoses connect immediately in front of the patient to a patient adapter for the selective connection of a breathing mask or a tracheal tube. The breathing gas hereby flows from a pressurized gas source through an inhalation valve to the patient, and from the latter through an exhalation valve outwardly into the atmosphere. The inspiratic breathing pressure is set and regulated at the inhalation valve; the expirational breathing pressure, the breathing frequency and the breathing phases at the exhalation valve. Special value is hereby set upon the timed control of the exhalation valve with adjustable breathing phases. The timing control device of the exhalation valve hereby consists of a system of pneumatic or electronic components. Disadvantageous therein are the high production and servicing costs which are connected with the extremely complex technical construction, as well as the uneconomically high gas usage. Moreover, the operation of these apparatuses is complicated and requires extensive experience, since the inspiratoric breathing pressure can not be preset at the inhalation valve. The actual pressure acting on the breathing passages is, namely, additionally dependent upon the set inhalation period and the flow of breathing gas. Any tampering with this sensible regulating circuit causes problems. In order to eliminate unnecessary danger to the patients, prior to each resetting of the apparatus, in particular prior to hand assisted breathing, the pressure which is set at the inhalation valve must be reduced, so as to be newly reset after effected resetting at a closed hose system on the basis of the breathing pressure measurement. This procedure is extremely complex and timeconsuming. A PEEP breathing is frequently, for example, in an embodiment which is offered for the breathing of newborn infants during transportation (Drager prospectus No. 5673.0), due to the lack of a continual expiratorial breathing gas flow, possible only with the aid of suitable auxiliary means (referring to German Published Patent Applications Nos. 2 241 291 and 2 406 679.) Due to the set forth reasons, these breathing apparatuses can only be utilized at pediatric intensive care stations having a high frequency of use and employing correspondingly educated professional personnel.

In another known manually or automatically controllable breathing apparatus (German Laid-open Patent Application No. 2 603 063) the breathing pressure is generated dynamically directly in the patient adapter through a gas jet tube into which breathing gas is introduced under a pressure of 0.25 to 2.5 atmospheres. The side of the patient adapter lying opposite to the tracheal tube is open to the atmoshphere, whereby the flow corss-section of the opening is equal to or larger than the flow cross-section of the tracheal tube so that during breathing phlegm can be aspirated from the breathing passageways of the patient. However, for newborn infants, contrary to the contentious in the mentioned published application, this is not possible without interruption of the breathing procedure due to the somewhat corresponding cross-sections of the suction hose and of the tracheal tube. The expiretorial dynamically generated static pressure in the patient adapter forms the exhalation valve. The breathing is controlled dependent upon pressure in the patient adapter proximate the connection for the tracheal tube, which is conducted by means of a sensor to a control apparatus which effects, through an inhalation valve, the inlet of the breathing gas and the breathing frequency. Upon the failure of the control valve a hand-assisted breathing, as is claimed, is not possible, inasmuch as with the control apparatus there fails the pressure restriction and there can build up an uncontrolled high static pressure in the lung of the patient. This breathing apparatus thus affords no advantages over the above mentioned apparatuses.

A known, only hand-operated breathing apparatus for infants is set forth by the so called breathing bag (Ambuprospectus Form No. 2500.11.75). It is inexpensive and thus finds widespread application. With it there can thus be carried out a periodic breathing corresponding to the breathing rhythm, however, there lacks a capability for blowing pressure, CPAP or IPPV-+PEEP breathing. The key magnitude breathing pressure is uncontrollably left to the sensing of the treating personnel, i.e.. The stronger the breathing bag is squeezed with the hand, the higher is the pressure generated in the breathing passages. At the small breathing volumes of newborn infants the indicated pressure safety is not effective. Based upon the set forth reasons, the breathing bag used for the breathing of newborn infants no longer conforms to the present state of the breathing technology, but is also dangerous in the hands of inexperienced personnel.

Pursuant to a further known manually operated breathing device (K. Riegel et al. in German Medical Weekly 99 (1974), 1624–1626), from which the present invention extends, the inspiratory breathing pressure controllable through a water column serving as an inhalation valve of from 0–40 cm $H_2O$ can be simply correlated with the needs of the newborn infant. The water column is arranged through a T-connector member intermediate a pressurized gas source for breathing gas and a patient adapter. The maximum inspiratory breathing pressure is limited by the immersion depth of the riser tube into the water level. When, due to the pressure which is pregiven by the riser tube, there is achieved a possible blowing up of the lung, the inflowing gas escapes completely through the water column. An important and dangerous disadvantage occurs when the hose leading to the water column is bent, so that an uncontrolled high pressure will then act on the lung. The continual breathing gas flow is preadjusted independently of the breathing pressure in accordance with need at the regulator for the infeed of breathing gas. The breathing is controlled by a free opening in the patient adapter which is in communication with the atmosphere and serves for exhalation. The cross-section of this opening corresponds to that of the breathing hose. A breathing-synchronized covering of this exhalation aperture with the finger leads to control breathing (IPPV). When the finger is positioned on the opening, for example, for 10 to 15 seconds, then there is reaching a blowing pressure breathing. This breathing apparatus presents a dependable system, until reaching the mentioned disadvantage, which has been used for many years in clinics. It contains no moving parts, is safe and easily installed, and also rapidly understandable by the layman. The magnitude of the key breathing pressure is hereby presettable in the apparatus. The sales price is like that of the breathing bag. The disadvantage of this apparatus is, above all, that no CPAP nor IPPV-+PEEP breathing can be effectuated, nor theraupeutically induced initial blowing pressure of between 40–70 cm $H_2O$ be effectuated since already at pressures of 40 cm $H_2O$ a water column as a pressure-limiting medium having an effective length of 90 cm is unwiedly.

Accordingly, it is an object of the present invention to so construct the above mentioned breathing apparatus with a simple and inexpensive construction that it will meet special needs in the breathing of newborn infants in a direct and dependable manner.

The foregoing object is achieved, by a first stage water column and an interconnectable second breathing stage as an inhalation valve consisting of the first column and an additional water column.

The foregoing object is further achieved by a choke arrangement in the exhalation opening of the patient adaptor as an exhalation valve whereby the cross-section of the choke arrangement as well as the quantity of the breathing gas introduced from the breathing gas source determine the value of the final expiratorial static pressure. In this manner, when a gas source is connected by way of a T-connector to the riser tube of the first column and to a ventable patient adapter, IPPV+PEEP— and CPAP-breathing can be freely adjustable and maintained and, as well, the pressure necessary for the initial unfolding of the patient's lungs is also provided for without risk of pneumothorax resulting from lung fissures and excess pressure.

The inventive breathing apparatus is constructed in two stages. The first breathing stage consists of the previously proven water column which concurrently forms a pressure-retaining valve for the inhalation valve. Hereby, the T-connecting member which interconnects the water column with the breathing gas source and the patient adapter through two breathing hoses, is rigidly interpreted in the riser tube. Any bending of the breathing hoses, irrespective as to location, can thereby no longer lead to an uncontrolled high pressure which would endanger the lung. Through the selective geometry of the arrangement, at a closed exhalation valve (inspiration) the inspiratory static pressure in the breathing passages to be generated, independent of the breathing gas flow is limited to a maximum of 30 cm $H_2O$. The interconnectable second breathing stage acts additively to the first and consists of a further water column which is connectable in series with the water column of the first breathing stage. By means of the second breathing stage there is thus possible an inspiratory blowing pressure of the lung of up to 60 cm $H_2O$.

An important element of the invention is a choke device, which is mountable on the patient adapter at the exhalation opening in communication with the atmosphere or fixedly connected with the patient adapter and, together with a closure element, forms the exhalation valve. Thus, during exhalation there can be constantly maintained a static pressure in the lung (PEEP/-CPAP), whereby the cross-section of the choke arrangement as well as the quantity of the breathing gas source determine the valve of the final expirational static pressure.

In a further advantageous embodiment of the invention this choke device is replaced by a pressure maintaining valve (corresponding to a water column) whereby the current static pressure is independent of the breathing gas flow.

The closure element formed by the hand-controlled breathing through the finger of the treating personnel: A not-closed exhalation opening corresponds to the CPAP breathing at a still obtained spontaneous breathing, periodic closing-off with the finger in accordance with frequency and breathing phases of the IPPV-+PEEP breathing, respectively, the blowing pressure breathing.

The breathing gas flow, thus, pursuant to the first embodiment has a dual function. Through it there is adjustable either the end expiratory breathing pressure by means of the water column of the first breathing stage, or the inspiratory breathing pressure by means of the second breathing stage, in effect, in the use of the second breathing stage, in a breathing apparatus pursuant to the first embodiment, a PEEP breathing is not possible.

Pursuant to an advantageous further modification there is generally achieved the capability of the PEEP breathing in that the choke device of the second breathing stage is also formed by a water column, which is connectable in series with the water column of the first breathing stage.

This embodiment is constructed, as well as in the first embodiment, in two stages wherein, however, all breathing stages merely include water columns which are connected in series and which act additive to each other. The connecting conduit between two water columns is advantageously so constructed that no bending can occur. In this manner the inspiratory breathing pressure in all breathing stages is independent of the breathing gas flow and is exclusively adjustable through the immersion depth of the riser tubes into the associated water levels, whereas the end expiratory breathing pressure is controllable exclusively through the breathing gas flow. Thus, in all breathing stages it is possible to have PEEP breathing. The further choke device pursuant to the first embodiment serves during its utilization merely to generate the end expiratory breathing pressure (PEEP/CPAP). It accordingly has only the function of a PEEP/CPAP valve and is advantageously fixedly integrated in the exhalation opening in the patient adapter or retrievably fastened to the patient adapter by means of a chain, since there is obviated the repositioning of a choke device as in the first embodiment.

Both water columns of the two stage breathing apparatus are suitably so designed that the first breathing stage allows for breathing pressures of up to, as a rule, the maximum required 30 mbar (corresponding to 30 cm $H_2O$), whereas the second breathing stage facilitates such of 30 mbar up to a maximum of 60 mbar.

Provided in the water column of the first breathing stage, in essence in the housing or the closure plug thereof, are advantageously two vent openings through which the gas streaming into the riser tube can flow out. One opening is in communication with atmosphere, the other with the riser tube of the water column of the subsequent second breathing stage. The second breathing stage is thus connectable only with the first breathing stage when the opening which is in communication with atmosphere is closed.

The water column of the second breathing stage, and as required, each subsequent breathing stage, in effect, the housing or the closure plug, advantageously evidences three openings. One opening is in communication through a sleeve with a displaceable riser tube closed at the upper end by means of a bore in the riser tube within the region of the sleeve. The sleeve length between the seals for the passing through of the riser tube corresponds to at least the adjustment range of the riser tube, or its displacement range. The two other openings serve for venting. Through these the gas streaming in through the riser tube can fully flow off. The one vent opening is hereby in connection with atmosphere. By means of the other, as needed, a further water column of a further breathing stage can be connected in series, wherein this further water column corresponds to the water column of the second breathing stage. The interconnection of each water column of a further breathing stage is effected in the same manner as the connection of the water column of the second breathing stage to that of the first breathing stage through a closure device for the vent opening leading to atmosphere.

Suitably, the connecting conduit between two sequential water columns is rigidly constructed and advantageously integrated into the housing connection of the water columns. Thusly, one hose connection is possible, however, care must be excercised that there is prevented a bending of this hose connection or the production of a water trap in the hose connection since this can lead to a pressure endangering the patient.

As mentioned, the presently following breathing stage is only connectable when a vent opening leading to atmosphere is closed. Suitably, the valve closure element therefore is hereby provided by a stopper which is retrievably fastened by means of a chain to the riser tube or the T-connector element attached to the former, so that the closure element can only be plugged in at a fully immersed riser tube in the water level (corresponding to 30 mbar in the first breathing stage) into a vent opening of the water column which is in communication with atmosphere of the current breathing stage for the connection thereto of the water column of the subsequent breathing stage. At inspiratory breathing pressures below the maximum value of the current breathing stage, 30 mbar in the first breathing stage, the closure element automatically sets free the vent aperture, since it is pulled out with the riser tube from the vent opening. This means that at pressures below this limiting pressure, the presently subsequent breathing stage is automatically separated. Inasmuch as the reanimation of newborn infants, on the basis of general recommendations, presently should already be commenced at inspiratory breathing pressures of maximum 20 mbar, there can thus be ensured that the second breathing stage is not inadvertently connected thereto or will remain connected.

Suitably, the closure element is also so constructed that, when during the downward sliding of the riser tube the closure element should inadvertently slide into the vent opening, a static pressure of below 5 mbar is already sufficient to press the closure element out of the vent opening.

Thereby it is also possible to so scale the riser tube of the water column of the subsequent breathing stage, such as the second breathing stage, that it commences with the final pressure of the currently preceding breathing stage, so that the subsequent stage can then only be connected to the preceding when the latter has reached its maximum pressure value, in the first breathing stage 30 mbar.

In order to avoid a mixup of scaled riser tubes, their diameters can be made different.

The embodiment with sleeve which is employed for the water column of the second and subsequent stage can also be utilized for the water column of the first breathing stage. The hose introducing the breathing gas, as well as the hose leading to the patient adapter, are then presently rigidly connected to the housing of the water column of the first breathing stage instead of to the riser. With that type of construction, the hoses need not be moved along during the adjustment of the pressure through the displacement of the riser tube.

In the automatically controlled embodiment, the closure element advantageously consists of a cylindrical tube and of a ball rotatable therein having a rotational axis perpendicular to the tube axis, wherein the ball is flattened on a side extending parallel to the rotational axis, and the cross-sections of the tube and ball are correlated with each other. The ball is driven by a compressed-air or battery-operated electric motor with controllable rotational speed whereby, for each rotation, there are traversed two breathing cycles. The breathing phases are not adjustable but are dependent upon the respective ball flattening.

The advantages which are achieved with the invention consist, in addition to the known and the interim reevaluated advantages, of a simplified and monitorable apparatus construction, particularly in that the embodiment which is manually controlled operates without disruption and requires no servicing since it evidences no movable components or valves which would thus be subjected to wear or to sticking; that patient and breathing apparatus which for manipulation and monitoring are required to be connected by only a single breathing hose, the breathing of newborn infants can be effected without risk in two stages, in which the inspiratory breathing pressure is preset on the apparatus and, in accordance with need, can be immediately changed, and the treating personnel can control the breathing type, frequency and phases directly on the patient through corresponding closing-off the exhalation opening in the patient adapter immediately with his finger without having to turn away from the patient. The otherwise necessarily complicated adjustments of the apparatus through a plurality of overseeable adjustable buttons and switches are thus also obviated, as well as the therewith connected risk of erroneous operation. In particular, an incorrect assembly or a bending of the breathing hoses will not lead to endangering of the patient.

The two-stage arrangement of the breathing sequence is particularly advantageous. Clinical experience over many years in the reanimation of newborn infants has thus shown that the breathing pressures must be principally variable, however, before anything pressures of over 30 cm $H_2O$ for newborns frequently lead to complications in the form of lung fissures and become therapeutically necessary only in exceptional instances and, in essence, exclusively for the initial unfolding of the lungs, in the normal case, however, such pressures of up to 30 cm $H_2O$ are adequate for the initial unfolding of the lung as well as for the artificial support of breathing.

The invention thus considers at first these significant clinical recognitions in the breathing technology of newborn known but not incorporated in any known breathing apparatus and, accordingly, divides the breathing sequence into two stages whereby the critical breathing pressure of 30 cm $H_2O$, in accordance with the action of a safety valve, forms the boundary between the first and second stage. The previously mostly employed, simple breathing apparatus, namely the breathing bag, operates with practically fixedly predetermined, moreover, uncontrollable pressures. Only with the expensive breathing apparatuses is the inspiratory breathing pressure continually adjustable between minimum and maximum pressures, without any kind of shutoff. Both, as mentioned, are dangerous. In the invention, the higher, dangerous breathing pressures of 30 to 60 cm $H_2O$ are normally blocked, with pressures maintained below 30 cm $H_2O$, and are only available through two undertaken manipulations, which represents an additional safety factor, and thereby protected from inadvertent utilization.

The first manipulation, in the first embodiment, consists of changing the choke device from the patient adapter to the vent opening of the water column which, however, does not alone permit for any pressure increase. First together with the second manipulation which is to be undertaken is it possible by means of the second breathing stage to come through increased breathing gas flows to high pressures. Hereby, in accordance with the required blowing pressure, breathing gas flows are necessary of up to 12 l/min. while in the first breathing stage such occur only at between 2 and 5 l/min. and depend upon the PEEP or CPAP which is to be set. After the effected unfolding of the lung, recognizable by the rising chest cage, the removal of the choke device from the vent opening of the water column alone ensures that the critical breathing pressure of 30 cm H₂O can no longer be exceeded and thereby further breathing effected without danger. Above all, with the utilization of the second breathing stage in the first embodiment, there must be sacrificed the PEEP breathing. Since thereby there should be carried out only the initial blowing pressure breathing for the unfolding of the lung, for which there are necessary only inspiratory but no end expiratory blowing pressures of the lung, this represents no disadvantage.

Additionally to the previously mentioned advantages, the advantages achieved in the second embodiment besides the mutual separately adjustable breathing pressures during the inspiration and expiration (inhalation and exhalation), consist in particular that in both breathing stages it is possible to have PEEP breathings. Furthermore, the (additional) choke device possesses only the function of a PEEP/CPAP valve and can be retrievably fastened on the patient adapter. Finally, the breathing apparatus is more handy and readily operable, and also safer in operation without causing the manufacture or the servicing to be more complex. In particular, an incorrect assembly or a bending of the breathing hoses will not lead to the endangering of the patient.

Finally, as the breathing apparatus pursuant to the second embodiment there can, moreover, be utilized as two-stage or multistage water vacuum meters and regulators for the thorax drainage. The series connection of a plurality of water columns is effected in the previously mentioned manner wherein, however, the vent openings of the water column of the first breathing stage in communication with atmosphere, which now forms the second or last suction stage, is not arranged in the housing thereof but as a vent opening in the water column of the second breathing stage which now forms the first suction stage, whereby this is analogously valid for a series connection of a plurality of water columns. Furthermore, the closure element for the vent opening which is located on the riser tube of the first breathing stage is now fastened on the riser tube of the first suction stage. Finally, the scales of the riser tubes are to be correspondingly changed in such a manner that the riser tube of the first suction stage now contains the scale of the riser tube of the first breathing stage, and so forth. Furthermore, the vacuum source and the patient are connected with the opening of the first suction stage serving as aspiration opening and which is in connection with atmosphere. The same concept, applies to a multistage construction.

Further features of the present invention may be ascertained from the following detailed description of an exemplary embodiment, elucidated in conjunction with the accompanying drawings in which schematically shown is that.

Figures 1, 2:
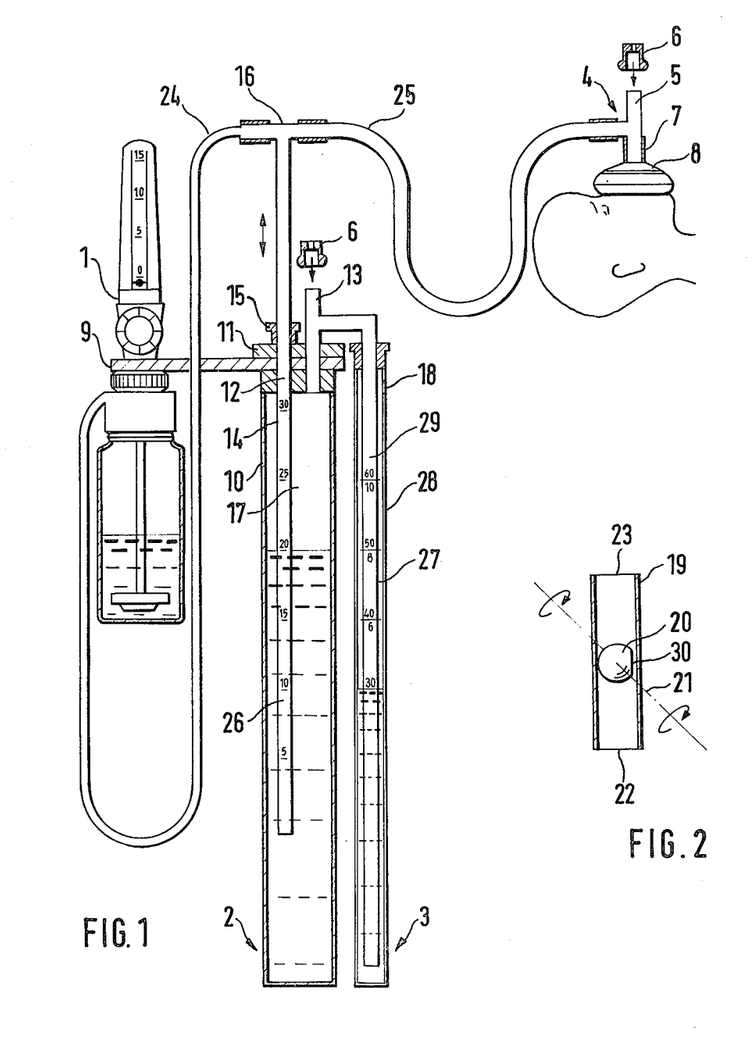
FIG. 1 illustrates a preferred embodiment of the invention.
FIG. 2 shows an enlarged view of a control valve.

As shown in FIG. 1, the breathing apparatus essentially consists of the usual flow-quantity regulator 1 for breathing gas with indication of the breathing gas flow in 1 l/min., of an inventive two-stage water column 2 with liquid manometer 3 and a patient adapter 4 having a choke 6 pluggable into the exhalation opening 5 as a choke device and a plug connector 7 for a face mask or, respectively, for a tracheal tube (not shown). The flow-quantity regulator 1 and the water column 2 are fixedly interconnected with each other through an adapter 9.

The two-stage water column 2 consists of a water vessel 10 filled with sterilized water up to the fill mark, which is formed, for instance, of acrylic glass which is sealed through a closure plug 11 with openings 12 and 13. The opening 12 serves to receive a scaled riser tube 14 of, for example, acrylic glass, which by means of an adjusting screw 15 can be fixed in a desired immersion depth. By way of the opening 13 the water receptacle 10 is vented. The riser tube 14, by means of a T-connector element 16 rigidly integrated in the riser tube 14, is connected to a pressurized gas source (not shown) for breathing gas through a breathing hose 24 through the flow-quantity regulator 1 and, additionally through a breathing hose 25 through the patient adapter 4 with the patient.

Figure 3A:
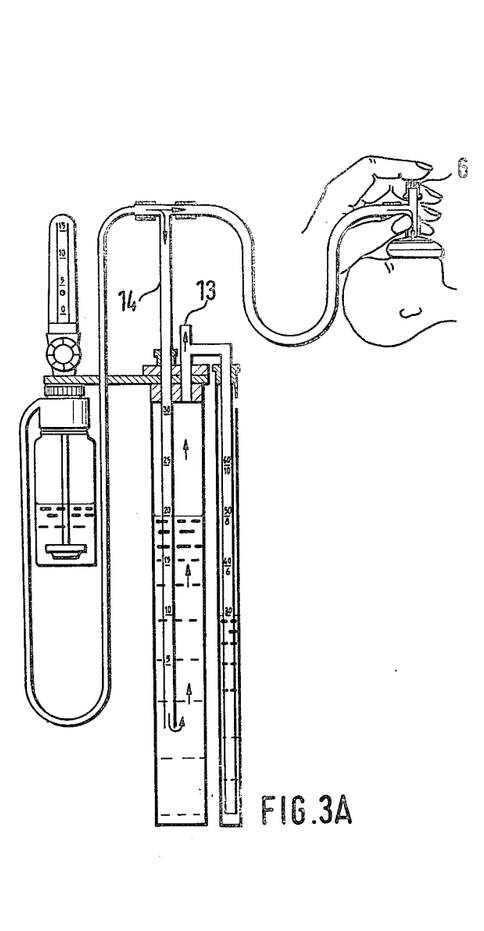
FIGS. 3 and 4 illustrate the artificial breathing of a patient with the embodiment of the invention illustrated in FIG. 1 with the utilization of only the first (FIG. 3) or additionally the second (FIG. 4) breathing stages, whereby arrows within the breathing gas conduits indicate the direction of the breathing gas flow during the inspiration (FIG. a) or, respectively, expiration (FIG. b)
Figure 3B:
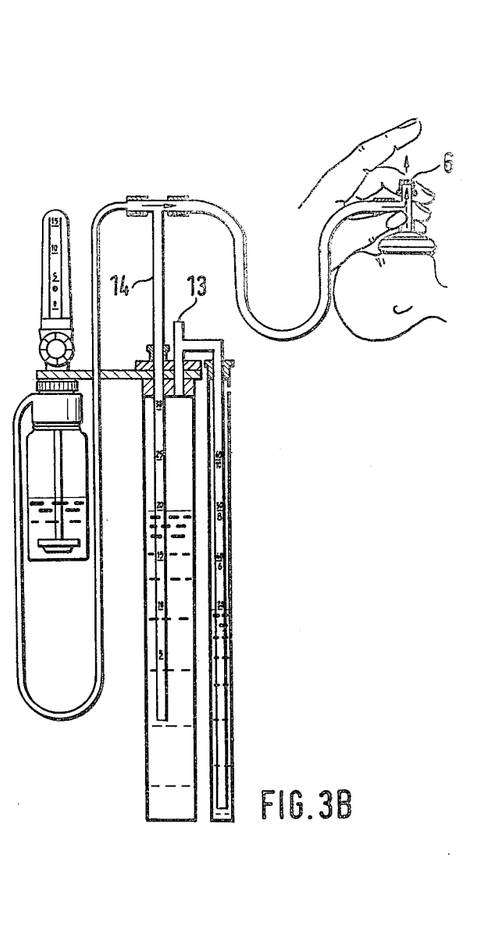

The inspiratory breathing pressure, in this elucidated first breathing stage, in which the free cross-sections of the vent opening 13 and the riser tube 14 generally correspond, is alone limited by the preadjusted immersion depth (maximum for example 30 cm ≙ breathing pressure of 30 cm H₂O) of the scaled riser tube 14 into the water level (FIG. 3a). When according to the pressure which is preset by the riser tube 14, there is reached the possible blowing up of the lung, then the streaming in breathing gas fully escapes across the water column 2 through the opening 13. The end expiratory breathing pressure (PEEP or, respectively, CPAP) is alone dependent upon the breathing gas flow through the choke 6 (FIG. 3b) with the choke 6 mounted on the exhalation opening 5. The actual static pressure which thus forms ahead of the choke 6 and thereby also in the breathing passages of the patient, can be read off on the scale 26 on the riser tube 14.

Figure 4A:
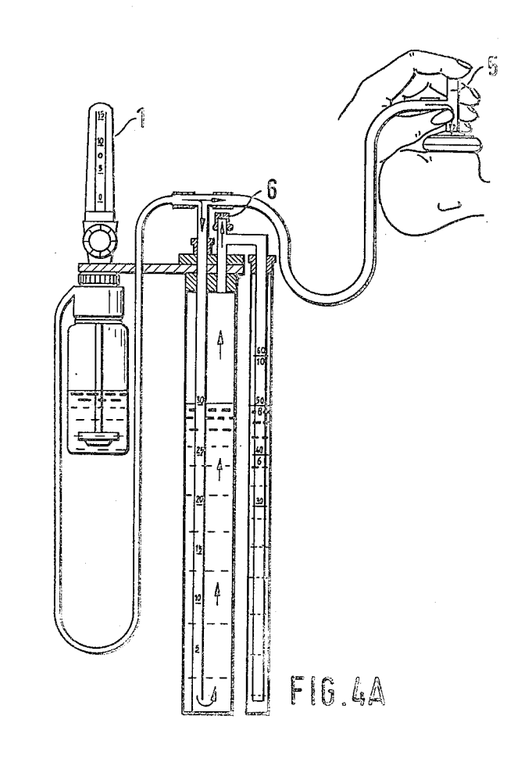
Figure 4B:
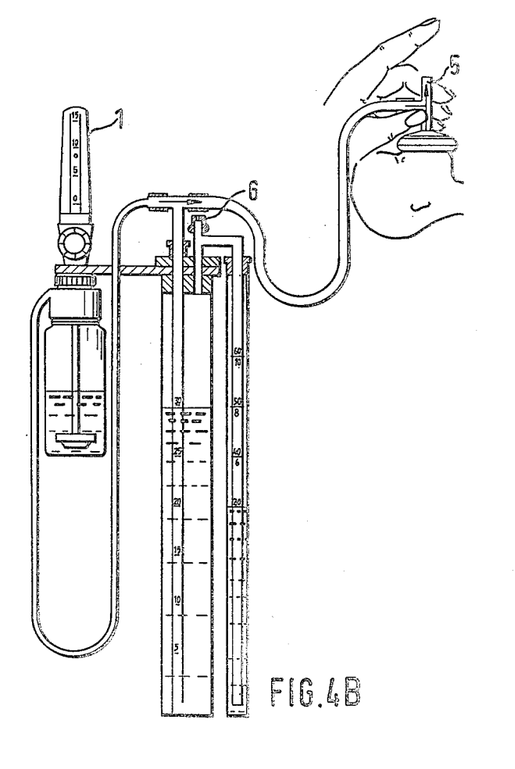

The second breathing stage expands the first and distinguishes therefrom by the choke 6 which is plugged on the vent opening 13 as the choke device (FIGS. 4a, 4b), whereby in the space 17 ahead of the choke 6 there is formed an additional static pressure which alone depends upon the breathing gas flow through the choke 6 and is indicated by the liquid manometer 3, as well as being limited to 40 cm H₂O. This dynamically generated static pressure adds itself to the hydrostatic pressure set at the riser tube 14. In this manner, with the second breathing stage there become possible breathing pressures of 30 to 70 cm H₂O, predetermined by the maximum immersion depth of the riser tube 14 in the water vessel 10.

The liquid manometer 3 consists of two acrylic glass tubes 27, 28 which are inserted into each other, are concentric and are sequentially connected in the type of a U-tube. The inner tube 27 is in communication with the chamber 17, the outer tube 28 through a bore 18 with the atmosphere. At an excess pressure in the chamber 17, the inner fluid column sinks whereas the outer rises correspondingly. The therewith associated breathing pressure is readable in cm $H_2O$ on the scale 29 on the outer tube 28, whereby the beginning of the scale (=the fill mark) is calibrated to the maximum immersion depth of the riser tube 14, here 30 cm. Below the current breathing pressure in cm $H_2O$ there is also indicated on the scale 29 the therefore necessary breathing gas flow in l/min. Through adjustment of the corresponding value on the flow-quantity regulator 1, there can also be preset the breathing pressure in the second breathing stage. As the fluid filling of the manometer can be utilized, as sold under the commercial designation chlorhexamed, a mouth and throat antiseptic-containing liquid which, on the one hand, acts as a disinfectant, and for another, due to its reddish color allows for good recognition of the liquid level.

FIG. 2 illustrates a control valve for an embodiment with automatic control. It consists of a cylindrical tube 19 and a ball 20 rotating therein, with a rotational axis 21 extending perpendicular to the tube axis whereby the ball, on a side parallel to the rotational axis 21 corresponding to the breathing phases, possesses a flattening 30. The ball is driven by a controllable motor (not shown). Through an opening 22, the control valve is mounted on the exhalation opening 5 of the patient adapter 4, whereby on an opening 23, depending upon need, there can be mounted the choke 6.

Figure 5:
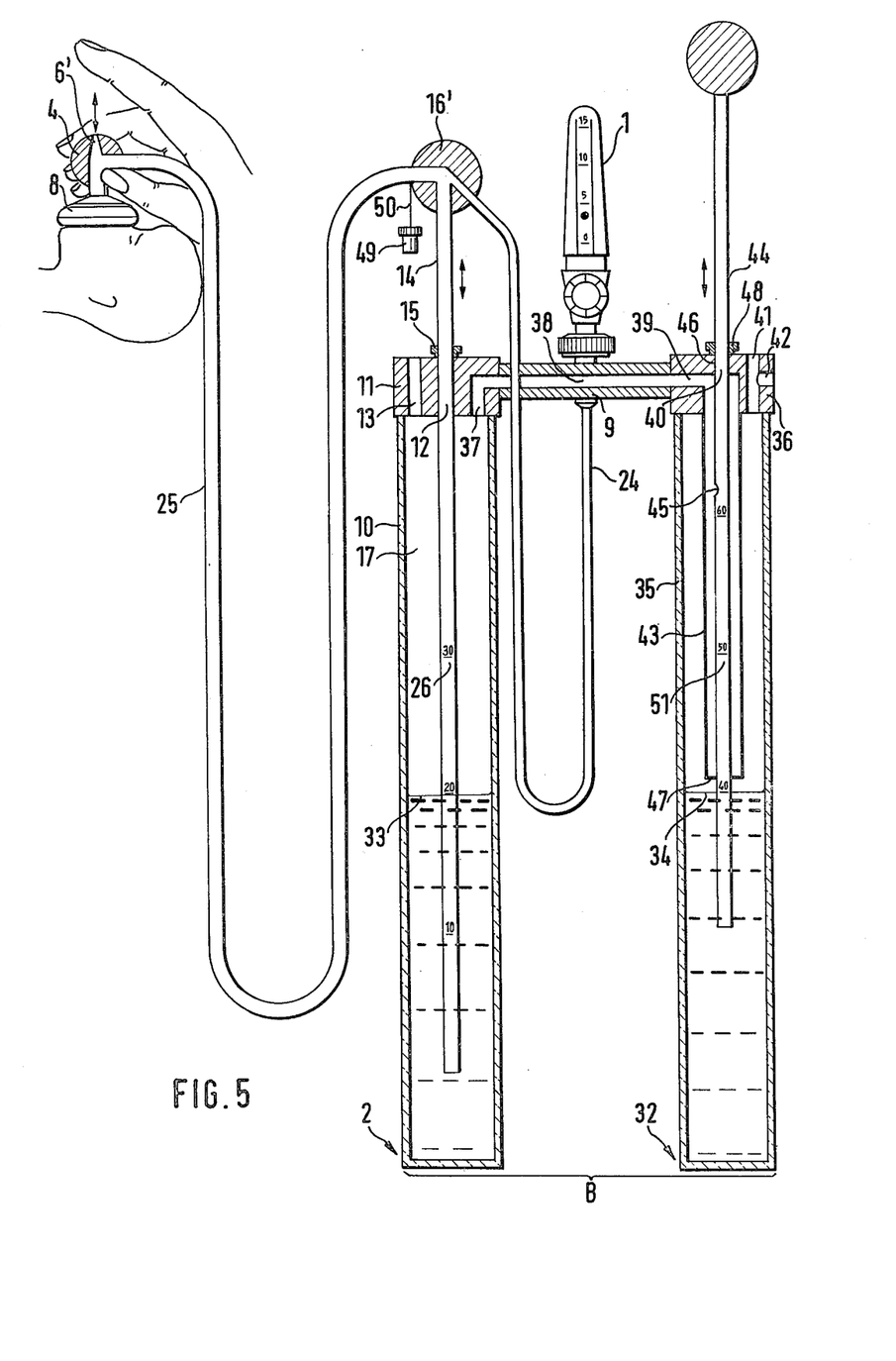
FIG. 5 is a second important embodiment of the invention.

The breathing apparatus B shown in FIG. 5 illustrates the second important embodiment which here is in two stages. The basic elements of each breathing stage are formed by water columns. In the elucidation of this embodiment there are employed the same reference numerals as in the description of the first embodiment (FIGS. 1–4) when this relates to the same constructional elements.

The inventive breathing apparatus B pursuant to FIG. 5 is usable in two stages in the illustrated embodiment. The basic elements of each breathing stage are formed by water columns.

The breathing apparatus B essentially consists of a flow-quantity controller 1 for breathing gas with indication of the breathing gas flow in l/min., a water column 2 at a first stage, connectable thereto a water column 32 for the formation of a second breathing stage, and a patient adapter 4 with a PEEP/CPAP choke 6' arranged in the exhalation opening thereof as a choke device, and a connector for a face mask 8 or, respectively, a tracheal tube (not shown). The flow-quantity regulator 1 and the water columns 2, 32 of the different breathing stages are rapidly connectable with each other through an adapter or a fastener 9.

The water columns 2, 32 of the two breathing stages consist of two essentially identical water receptacles 10 or 35 of, for example, acrylic glass, fillable up to a fill mark 33 or 34 with sterilized water, in which there is inserted an outwardly sealed closure stopper 11 or 36, which are, for instance, threaded in. The closure stoppers 11, 36 are suitably rigidly connected with the fastener 9, or even integrally formed therewith.

The closure stopper 11 of the water column 2 of the first breathing stage possesses openings 12, 13, 37. The opening 12 serves for the sealed passing through of a scaled riser tube 14 formed, for example, of acrylic glass, which by means of an adjustment screw 15 can be fixed in a desired immersion depth. The opening 13 is in communication with atmosphere. The chamber 17 of the water column 2 above the marking 33 is vented through this opening 13. Through the opening 37, the chamber 17 is in communication, by means of a connecting conduit 38, with the water column 32 of the second breathing stage.

The riser tube 14 is connected by a T-connector element 16', which is rigidly integrated in the riser tube 14, on the one, through a breathing hose 24 across the flow-quantity regulator 1 with a pressurized gas source for breathing gas (not shown) and, on the other, through a breathing hose 25 with the patient adapter 4 and across the latter with the patient.

The closure stopper 36 of the water column 32 of the second breathing stage possesses openings 39, 40, 41, 42. The opening 39 leads into a sleeve 43 in which the riser tube 44, which is closed at its upper end, is displaceable exteriorly sealed. The sleeve 43 need not be transparent and, for example, can be formed of a brass tube or the like. Within the sleeve 43, the displaceable riser tube 44 evidences an opening 45 through which the interior of the riser tube is in communication with the chamber 17 of the water column 2 of the first breathing stage. It is valid for the length of the sleeve 43 that the adjusting range, in essence, the displacement range of the riser tube 44 in cms water column (corresponding mbar) corresponds to the sleeve length in cms between the seals 46 and 47. The opening 40, together with the seal 46 and the seal 47 serves for the exteriorly sealed passing through of the riser tube 44. There can also be provided an adjustment of screw 48. The openings 41 and 42 serve for venting. Through these, the gas which streams through the riser tube 44 into the second water column 32 can fully flow off. Through the opening 42 there can additionally be connected on in series a further water column corresponding to a further breathing stage.

In order to avoid an inadvertent bending of the connecting conduit 38 between the water columns 2 and 32, this is rigidly constructed and in the illustrated embodiment integrated in the fastening 30 for the two water columns 2, 32 or, respectively, their closure stoppers 11, 36.

It is mentioned that the water column 2 of the first breathing stage can evidence the same construction as the water column 32 of the second stage, in effect, with infeed through a sleeve encompassing the riser tube. In such an instance, the T-connector element 16' is rigidly attached to an inlet opening in the closure stopper 11 and need no longer be moved together with a displacement of the riser tube 14.

The interconnection of the water column 32 of the second breathing stage with the water column 2 of the first breathing stage is effected through the closing of the vent opening 13 in the closure stopper 11 of the water column 2 of the first breathing stage. Suitable hereby as the closure element is, in particular, a stopper plug 49. In order to prevent the stopper 49 to be inserted into the vent opening 13 prior to the maximum pressure achievable by the water column 2 of the first breathing stage has actually been reached, the stopper 49 can be retrievably fastened through a chain 15 on the T-connector elements 16', or directly on the riser tube 14, so that the stopper 49 can be inserted into the opening 13 only at a fully immersed riser tube 14. This is effected through suitable dimensioning of the chain 50.

In such a case, the riser tube 44 of the subsequent water column 32 can also incorporate a scale 51 which begins with the maximum pressure value attainable through the water column 2 of the first breathing stage (for example, 30 mbar). In order to avoid the mixing up of scaled riser tubes, these are suitable so constructed that they are presently employable only in the water column of the therewith associated stage. Suitable are different cross-sections.

The vent openings in the closure stoppers can be constructed separately as in the closure stoppers 11, or as in the closure stopper 36 commonly, for example, as T-shaped constructions. It should be merely ensured that the venting of the final water column of the breathing stages in operation cannot be inadvertently prevented. The inspiratory breathing pressure, in this elucidated preferred embodiment of the invention—as shown in FIG. 5—, is alone limited by the preadjusted immersion depth (maximum for example every 30 cm=breathing pressure of 30 cm $H_2O$=30 mbar) of the scaled riser tube 14, 44 into the water level 33, 34. When according to the pressure which is preset by the riser tube 14, 44, there is reached the possible blowing up of the lung, then the streaming in breathing gas fully escapes across the water through the opening 13 or 41, 42—forming bubbles.

The first breathing stage operates at pressures not exceeding 30 cm $H_2O$. The second breathing stage can be switched in with the aid of the stopper 49. When pressures of the first and the second units are added, the apparatus may deliver respiration pressures ranging from 30 cm $H_2O$ up to 60 cm $H_2O$. When the breathing apparatus operates at pressures below 30 cm $H_2O$ the second breathing stage is switched off automatically.

The final expiratory breathing pressure (PEEP, CPAP) is alone dependent upon the variable breathing gas flow through the choke 6'. The actual static pressure which is formed ahead of choke 6' and thereby also in the breathing passages of the patient, can be read off on the scale 26 on the riser tube 14.

The expiration is controlled by closing (=inspiration) and opening (expiration) of the expiration opening (using the integrated PEEP/CPAP choke 6') in the patient adapter 4 with one finger of that hand which holds the patient adapter 4 or the respiration mask 8 to the face of the patient in those cases in which the mask has to be applied.

Figure 6:
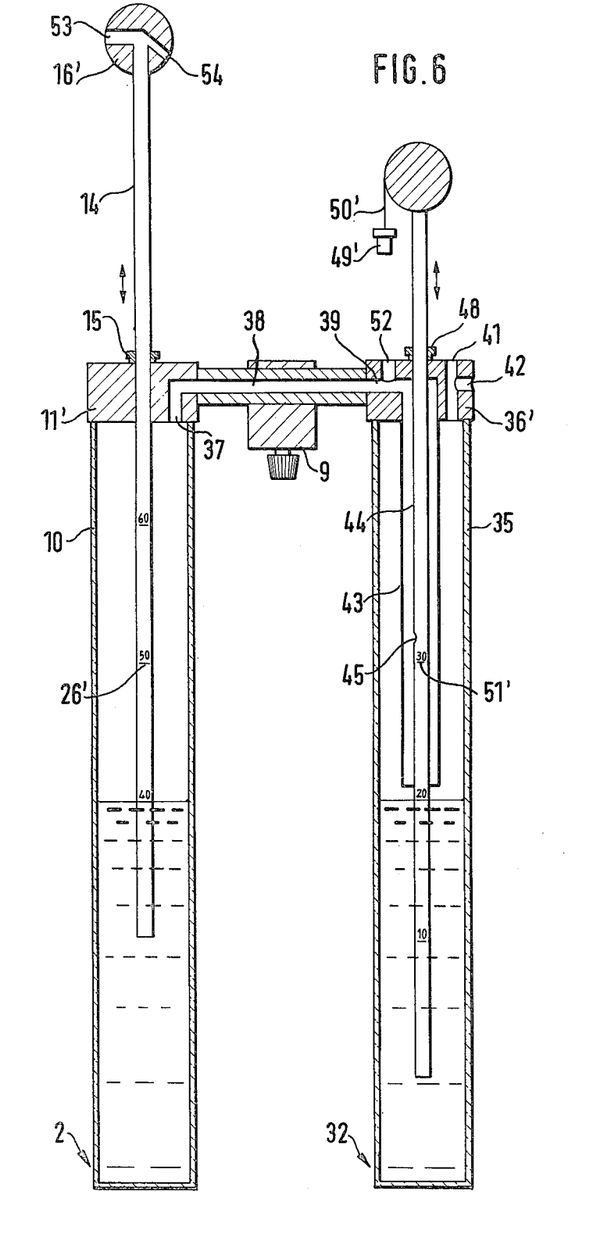
FIG. 6 illustrates a breathing apparatus during utilization in thorax drainage.

FIG. 6 essentially shows an apparatus having the same construction as in FIG. 5 in which, however, the apparatus pursuant to FIG. 6 is constructed as a water vacuum regulator and meter for thorax drainage.

In this apparatus the water column 32 forms the first suction stage, and the water columns 32 and 2 together form the second suction stage. By means of the vent openings 41, 42 of the water column 32 there is now connected a vacuum source, in essence, to a conduit leading to the patient. A stopper 49' is connected to the riser tube 44 of the water column 32 by means of a chain 50'. Provided in the closure stopper 36' is, additionally, an opening 52 which is closable by means of the stopper 49', through the riser tube 44 being inserted into the water column, or the housing 35 thereof whereby, for the formation of the second suction stage, the water column 2 is connected thereto. The water column 2, at its T-connector element 16' no longer includes connecting conduits 24 or 25, but allows for a connection to environmental air through the released opening 53, 54 in which there were inserted the connecting hoses 24 and 25 pursuant to FIG. 1. Furthermore, the inlet opening 13 is no longer provided in the closure stopper 11'. Furthermore, there is to be determined that the riser tubes 44 and 14 incorporate scales 51' or, respectively, 26' which distinguish from the scales 51 or 26 pursuant to FIG. 5, particularly possess mutually interchanged scale ranges.

The vacuum source which is connected to one of the openings 41, 42 produces a subpressure in the patient which, through the displacement of the riser tube 14 in the water column 42 in the first suction stage, is limited to a value readable on the scale 51'. When at the maximum attainable subpressure limited by the water column 32, in effect, at a riser tube 44 fully inserted into the water column 32, there is required a still higher vacuum, then the stopper 49' is inserted into the opening 52 so that the water column 2 is interconnected for the formation of the second suction stage.

It is mentioned that, on the one hand, also here the water column 2 can have a construction comparable with the construction of the column 32 (sleeve in the closure stopper, therein an externally sealed displaceable riser tube, and an opening in the riser tube within the sleeve). Furthermore, the closure stopper 36' of the water column 32 can, in lieu of the openings 41, 42, include merely one thereof, wherein a T-connector element is inserted therein by means of which there is attainable the connection between the vacuum source and the patient, similar to an embodiment in which there is described the breathing apparatus B pursuant to FIG. 5. Finally, the apparatus pursuant to FIG. 6 can alsio be multistage constructed, for example, in that by means of the openings 41 and 42 through a connecting conduit corresponding to the connecting conduit 38, a further water column which corresponds in construction to the water column 32 is connected thereto, so that this water column now forms the first suction stage, and so forth. In a construction of all water columns such as the water column 32, the connection is possible of further water columns at both sides.

Also here is there merely to be ensured that in the last water column of the suction stage in operation there is also prevented an only inadvertent closure of the opening which stands in communication with environmental air (here the openings 53 and 54).

It is to be mentioned that, naturally, the construction of the closure stoppers can be so as to be suitable for both types of operation. In such an instance, in dependence upon operation, either the opening 52 during utilization as a breathing apparatus pursuant to FIG. 5, or in the opening 13 during utilization for thorax drainage must be closed off through suitable means.

What is claimed is:

1. In a breathing apparatus for reanimation of newborn infants, comprising a breathing gas source, a patient adaptor an an inhalation valve assembly, said inhalation valve assembly comprising a first water column tube having an open upper end, first cover means mounted over said open upper end of said first water column tube and including a passageway communicating the interior of said first water column tube to atmosphere, a first riser tube slidably and adjustably mounted through said first cover means, said first riser tube having a first end adapted to be located within said first water column tube below the level of water therein and an opposite second end extending exteriorly of said first water column tube, a T-connector element, said second end of said first riser tube being connected to a first leg of said T-connector element, said patient adaptor including first, second and third ports, said first port including means for providing an oronasal flow of breathing gas to a patient, said second port comprising a closable opening for providing free exhalation to the atmosphere, a breathing hose connected between said third port and a second leg of said T-connector, conduit means connected between said breathing gas source and a third leg of said T-connector, regulator means associated with said breathing gas source for adjusting the quantity of the breathing gas source; the maximum immersion depth of the first riser tube determining the maximum inspiratory breathing pressure; the improvement comprising a second water column tube connectable in series with said first water column tube, said second water column tube having an open upper end, said cover means mounted over said open upper end of said second water column tube and including a passageway communicating the interior of said second water column tube to atmosphere, a second riser tube slidably and adjustably mounted through said second cover means, said second water column tube having a first end adapted to be located within said second water column tube below the level of water therein and an oppositely closed second end extending exteriorly thereof, said second riser tube further including a gas inlet port located intermediate the ends thereof, rigid connecting conduit means connected to said first and second cover means and providing a sealed gas flow path between the interior of said first water column tube and said gas inlet port of said second riser tube, means for selectively occluding the passageway in said first cover means, whereby said riser tubes of said water column tubes being independently adjustable and, by occluding the passageway in said first cover means, the integration of the first and second water column tubes provides a variable and controllable inspiratoric breathing pressure.

2. Breathing apparatus according to claim 1, including fastening means for connecting said water column tubes and regulator means together and wherein the connecting conduit means is in said fastening means for the water column tubes and the regulator means.

3. Breathing apparatus according to claim 1, wherein at least the first cover means of the first water column tube includes two outlet openings of which one serves for connection with the rigid connecting conduit means and the other serves as said passageway closable for the operation of said second water column tube only when the first water column tube has reached its maximum pressure value.

4. Breathing apparatus according to claim 3, wherein said means for occluding includes a stopper for closing the other outlet opening.

5. Breathing apparatus according to claim 4, wherein the stopper is fixedly connected with the first riser tube of the first water column tube.

6. Breathing apparatus according to claim 1, wherein said rigid connecting conduit means includes a sleeve which encompasses said second riser tube of said second water column tube, and said inlet port being located in the second riser tube such that it opens over the entire range of displacement of the second riser tube corresponding to the adjustment range within the sleeve.

7. Breathing apparatus according to claim 1, including choke means having a choke passage therein selectively mounted on said second port of the patient adapter for determining the end expiratory breathing pressure wherein the cross-section of the choke passage, being substantially smaller than that of the patient adaptor, and whereby, and the quantity of the breathing gas introduced from the breathing gas source determines the value of the end expiratory static pressure.

8. Breathing apparatus according to claim 7, wherein the choke means is fixedly connected with the patient adapter.

9. Breathing apparatus according to claim 8, wherein the choke means is integral with the patient adapter.

10. Breathing apparatus according to claim 7, wherein the closable opening of the second port of the patient adapter consists of a tube having a cross-section which is cyclically adjustable between a maximum value and a zero minimum value.

11. Breathing apparatus according to claim 10, including an ball having a flattening being located in the tube and in conformance with the cross-sectional dimensions of the tube, said ball being cyclically rotatable about an axis essentially parallel to the flattening.

12. Breathing apparatus according to claim 10 or 11, including a adjustable motor with regulatable rotational speed for rotating said ball.

13. Breathing apparatus according to claim 1, including a scale on each riser tube corresponding to the breathing pressure values.

14. Breathing apparatus according to claim 13, wherein for scaled riser tubes, the riser tubes of each different water column tubes are so differently constructed that they are only employable at that water column tube.

15. Breathing apparatus according to claim 14, wherein the riser tubes have differing cross-sections.

16. Breathing apparatus according to claim 1, wherein the T-connector element is rigidly connected with the first riser tube in the first water column tube.

17. Breathing apparatus according to claim 1, including a scale on the vessel of the water column corresponding to the breathing pressure values.

* * * * *